United States Patent [19]

Hsu

[11] Patent Number: 5,958,417
[45] Date of Patent: Sep. 28, 1999

[54] HERBAL COMBINATIONS

[76] Inventor: Chau-shin Hsu, 6380 Sheri La., Long Beach, Calif. 90815

[21] Appl. No.: 08/736,392

[22] Filed: Oct. 24, 1996

[51] Int. Cl.⁶ .................................................... A61K 35/78
[52] U.S. Cl. ........................................................... 424/195.1
[58] Field of Search .......................................... 424/195.1

[56] References Cited

U.S. PATENT DOCUMENTS 5,595,743   1/1997   Wu ........................................ 424/195.1

OTHER PUBLICATIONS

CR–201 (Jiang Zhi) Natural Cholesterol Management, presented by ProBotanixx, dated approximately Sep. 1996.

*Primary Examiner*—Mary E. Ceperley
*Attorney, Agent, or Firm*—Robert D. Fish; Crockett & Fish

[57] ABSTRACT

Herbal combinations which reduce serum cholesterol and triglyceride levels comprise (1) herbs having substantial recognized activity in enhancing circulatory function (ECF herbs) and (2) herbs having substantial recognized effects in promoting bowel motility (PBM herbs). Preferred combinations have a combined total of at least 16% (dry weight basis) of at least two ECS herbs in combination with a combined total of at least 16% (dry weight basis) of at least two PBM herbs. Particularly preferred combinations are selected from the following herbs: Crataegus, Ho Shou Wu, Chrysanthemum, Lotus Leaf, Alisma and Hu-Zhang, Cassia Seed, and Rhubarb.

1 Claim, 3 Drawing Sheets

| Common Name | Exemplary Latin Name | Pinyin | Actions | CR-201 | Range |
|---|---|---|---|---|---|
| Crataegus | Crataegi Fructus | *Shan Zha* | Reduces hypercholesterolemia, angina pectoris, and hypertension. Promotes digestion and removes food stagnancy. | 20% | 8-30% |
| Ho Shou Wu | Polygoni Multiflori Radix | *He Shou Wu* | Increases peristalsis in the large intestine, decreases absorption of cholesterol, increases cellular antioxidants. | 12% | 8-25% |
| Cassia Seed | Cassiae Torae Semen | *Jue Ming Zi* | Acts as an asperient, antiasthenic, laxative, and diuretic agent. | 15% | 8-25% |
| Chrysanthemum | Chrysanthemi Flos | *Ju Hua* | Increases coronary vasodilatation and coronary blood flow. | 10% | 0-13% |
| Lotus Leaf | Nelumbinis Folium | *Lian Ye* | Inhibits the elevation of total and free cholesterols, relaxes smooth muscles and lowers blood pressure. | 10% | 0-13% |
| Alisma | Alismatis Rhizoma | *Ze Xie* | Promotes urination, affects hydrolysis of lipids and formation of acetyl CoA. | 15% | 8-30% |
| Hu-Zhang | Polygoni Cuspidati Rhizoma | *Hu Zhang* | Increases myocardial contractility and coronary circulation. | 10% | 8-20% |
| Rhubarb | Rhei Rhizoma | *Da Huang* | Promotes bowel movements and removes accumulation from the digestive tract. | 8% | 0-10% |

FIGURE 1

|  | CR-201 (*Jiang Zhi*) | Western Pharmaceutical Drugs |
|---|---|---|
| Side Effects | none/minimal | carcinogenic |
| All Natural Ingredients | yes | no--synthetic chemicals |
| Cost (per month) | $59.85 (max. dosage) | $71.65-$88.10 |
| Cost (per year) | $718.20 | $859.80-$1057.20 |
| Availability | through licensed practitioners | by prescription only |
| Long-Term Maintenance | yes--poses no danger for long-term problems | no--prolonged intake exacerbates long-term side effects |
| Additional Benefits | can be used in conjunction with weight management program | none |

Figure 2

HERBAL COMBINATIONS

I. FIELD OF THE INVENTION

The field of the invention is herbal combinations.

II. BACKGROUND OF THE INVENTION

Coronary heart disease (CHD) is the leading cause of death for both men and women in the United States, accounting for approximately 500,000 deaths each year. A significant percentage of CHD is associated with abnormal cholesterol and triglyceride levels, and numerous pharmaceuticals have been developed to treat these conditions. Unfortunately, some of the most popular cholesterol and triglyceride lowering pharmaceuticals, including statins (lovastatin, pravastatin, simvastatin, and fluvastatin) and fibrates (gemfibrozil, marketed as Lopid), have been linked to undesirable side effects. For example, recent clinical studies have indicated that these drugs can be carcinogenic. Lovastatin was reported to cause excess stomach, liver, and lung tumors in mice, and the other statins reviewed were said to cause rodent cancers. Gemfibrozil was reported to cause liver cancers in mice.

One possible solution for reducing toxicity is to use herbal formulations rather than purified pharmaceuticals. Herbs have been used throughout the world for many conditions, including circulatory conditions, and there is at least some evidence that herbal remedies may tend to have less deleterious side effects than corresponding pharmaceuticals.

There are, however, numerous problems encountered in using herbs in the treatment of medical conditions. One such difficulty is that a single herb may contain a multitude of active, and sometimes conflicting components. The common herb, rhubarb, for example, causes constipation in small doses because of its tannic acid component, but is a potent laxative in larger doses because of other components. Additional potential difficulties arise from plant-to-plant variation in the concentration and activity of active components.

Moreover, the situation is considerably exacerbated with respect to herbal combinations. In addition to the above-mentioned problems, combinations raise the possibility of synergistic effects among components in the various herbs, and increase the difficulties associated with anticipating and analyzing side effects.

Many herbs are reported to have substantial effects on the circulatory system. Herbs within this group include, for example, Ho Shou Wu (*Polygoni multiflori radix*), which reportedly decreases absorption of cholesterol from the intestines, Chrysanthemum (*Chrysanthemi flos*) and Hu-Zhang (*Polgoni cuspidati rhizoma*) which reportedly increase coronary circulation, Lotus leaf (*Nelumbinis folium*) which reportedly inhibits the elevation of total and free cholesterol, and Alisma (*Alisma rhizoma*) which reportedly improves hydrolysis of lipids.

Many herbs are also reported to have substantial effects on the digestive tract. Herbs within this group include, for example, Crataegus (*Crataegi fructus*), which reportedly promotes digestion, Cassia Seed (*Cassiae torae semen*), which reportedly acts as a laxative, and Rhubarb (*Rhei rhizoma*), which reportedly promotes bowel movements and removes accumulation from the digestive tract.

While many effects of individual herbs are known, it is often unclear in the art which herbs to combine, and in which percentages, to achieve improved results. It is especially unclear in the art which herbs, and in what combinations, one would combine the herbs to enhance reduction in serum cholesterol and triglyceride levels.

III. SUMMARY OF THE INVENTION

The present invention is directed to cholesterol and triglyceride reducing herbal combinations comprising (1) herbs having substantial recognized activity in enhancing circulatory function (ECF herbs) and (2) herbs having substantial recognized effects in promoting bowel motility (PBM herbs).

Preferred combinations have a combined total of at least 16% (dry weight basis) of at least two ECF herbs in combination with a combined total of at least 16% (dry weight basis) of at least two PBM herbs. In particularly preferred combinations the ECF herbs are selected from Crataegus, Ho Shou Wu, Chrysanthemum, Lotus Leaf, Alisma and Hu-Zhang, and the PBM herbs are selected from Crataegus, Ho Shu Wu, Cassia Seed, and Rhubarb.

Various objects, features, aspects, and advantages of the present invention will become more apparent from the following detailed description of preferred embodiments of the invention, along with the accompanying drawings.

IV. BRIEF DESCRIPTION OF THE DRAWINGS

FIG. 1 is a table of exemplary combinations according to the present invention.

FIG. 2 is a table comparing benefits and costs of a preferred combination against selected pharmaceuticals.

V. DETAILED DESCRIPTION

Figure 3:
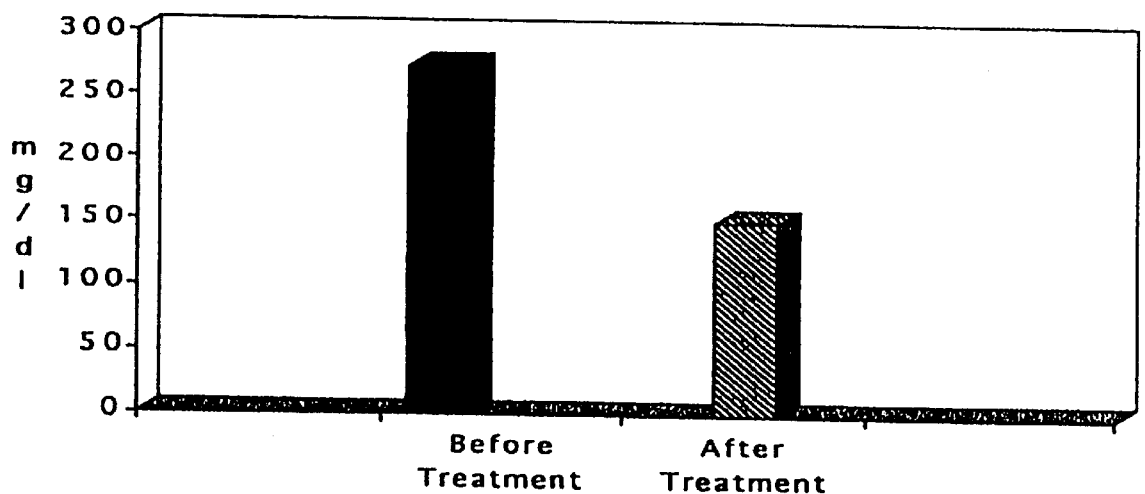
FIG. 3 is a graph showing change in triglyceride levels of human patients after administration of a preferred combination according to the present invention.

Referring first to FIG. 1, the table lists eight types of herbs which are contemplated to be included in one or more of the claimed combinations. Columns one through four provide basic identifying information for the various types of herbs, while columns five and six provide preferred combinations of those types. In particular, the first column sets forth common names of the herbs, the second column sets forth Latin names of a representative member of the respective genus, the third column sets forth the transliterated Chinese common names, the fourth column sets forth important medicinal characteristics of the herbs, the fifth column sets forth percentages of the herbs included in the most preferred combination, while the sixth column sets forth preferred ranges of herbs found in exemplary combinations.

All formulation percentages herein are given as dry weight percent of the normally used medicinal part of the herb. The following descriptions further clarify the herbs listed in the table of FIG. 1.

Crataegus is generally known in the West as hawthorn (Crataegus oxyacantha). Crataegi are usually encountered as a tree or a bush, and the normally used medicinal parts are the flowers and the fruit. The active principles are reported to be chlorogenic acid, caffeic acid, citric acid, crataegolic acid, malinic acid, ursolic acid. Crataegus is used to treat hypercholesterolemia, angina pectoris, and hypertension. Chinese medicine considers Crataegus to be useful in reducing food stagnancy and blood stasis.

Ho Shou Wu is a perennial which grows one to three feet high. One species is known in the West as Solomon's Seal, and the normally used medicinal part of the plant is the rootstock. The active principles are reported to be chrysophenol, emodin, emodin methyl ester, rhein, and the glycoside rhaphantin. Ho Shou Wu has traditionally been used as a laxative which lowers plasma cholesterol by decreasing its absorption.

Cassia is an annual plant of the Leguminosae family. The normally used medicinal part is the seed. Cassia seed is reported to contain many active substances, including chrysophenol, emodin, aloe emodin, rhein, physcion, obtusin, aurantioobtusin, chrysobtusin, rubrofusarin, norrubrofusarin, toralactone, obtusifolin, rubrofusarin gentiobioside, torachrysone, carotin and glycosides. Cassia seed has been used to treat hypercholesterolemia and hypertension. In traditional medicine, Cassia seed was used to remove "heat" from the liver, improve visual acuity, and as a laxative.

Chrysanthemum is a common flowering plant, and the normally used medicinal part is the flower. The active substances are reported to be bornol, chrysanthenone and camphor. Chrysanthemum has been used to treat angina pectoris and hypertension and hypercholesterolemia. In China, chrysanthemum is used to clear the eye and the mind, as well as an antitoxin. Chrysanthemum is also widely used as a remedy for the common cold, headache, dizziness, red eyes, swelling, and hypertension.

Lotus is a member of the family that includes the common water lily. The normally used medicinal part is the leaf, which is reported to contain several alkaloids including nuciferine, roemerine, O-nornuciferine, anonine, lirodenine, dihydronuciferine, anneparine, N-methylcoclaurine, and N-methylisococlaurine. Lotus leaf is used to disperse body heat and is said to increase essential body energies, in particular those of the defensive systems. The alkaloids said to have a relaxing effect on smooth muscles, and thus to lower blood pressure.

Alisma is a perennial plant with small, white, umbrella-shaped flowers. The normally used medicinal part is the root or tuber. The active substances are reported to be triterpenoids, alisol A, B, and C, alisol monoacetate, sugars, Amino acids, and essential oil epialisol A. Alisma has been shown in clinical trials to lower plasma cholesterol levels, protect hepatic function, and increase the urinary excretion of Na, Cl, and urea. Alisma is said to affect hydrolysis of lipids and to decrease the formation of acetyl CoA. A combination of *Crataegi fructus* and *Alisma rhizoma* given to patients with hyperlipidemia produced significant decreases in serum cholesterol and triglyceride levels, along with an increase of HDL cholesterol.

Hu-Zhang is a perennial bush with green, white and red flowers. The normally used medicinal parts are the stem and tuber. The active principles are said to include several glucosides, anthroquinones, flavonoids, and organic acids such as oxalic and tartaric. Hu-Zhang has been used medicinally to lower blood cholesterol levels, and to increase myocardial contractility and coronary circulation.

Rhubarb is a perennial herb which is grown both for nutritive and ornamental purposes. The normally used medicinal part is the rootstock. The active components are anthraquinones and their monoglucoside derivatives, Dianthraquinones, Naphtalins, as well as gallic acid, glucogallin, rheum tannic acids, catechol, and cinnamic acid. Rhubarb can stimulate the secretion of bile acid, and the rhubarb polyglycosides can significantly decrease levels of serum and liver total cholesterol. Rhubarb has long been used in Chinese medicine to treat constipation, especially when due to high body temperature. It is also used in small doses to treat chronic diarrhea, indigestion, and acute intestinal infections, such as appendicitis and peritonitis, ileitis, and acute hepatic jaundice. Rhubarb is also effective in gallstone removal and in cholecystitis. As an adjuvant agent, Rhubarb is used as a hemostatic in hempotysis, ulcer hematemesis, ulceration of the oral mucosa, ulcerative wounds, and so forth.

FIG. 2 is a table comparing especially preferred embodiments of the claimed combinations (CR-201 and variants) with modern anti-hyperlipidemia pharmaceutical combinations. The table is self explanatory.

Figure 4:
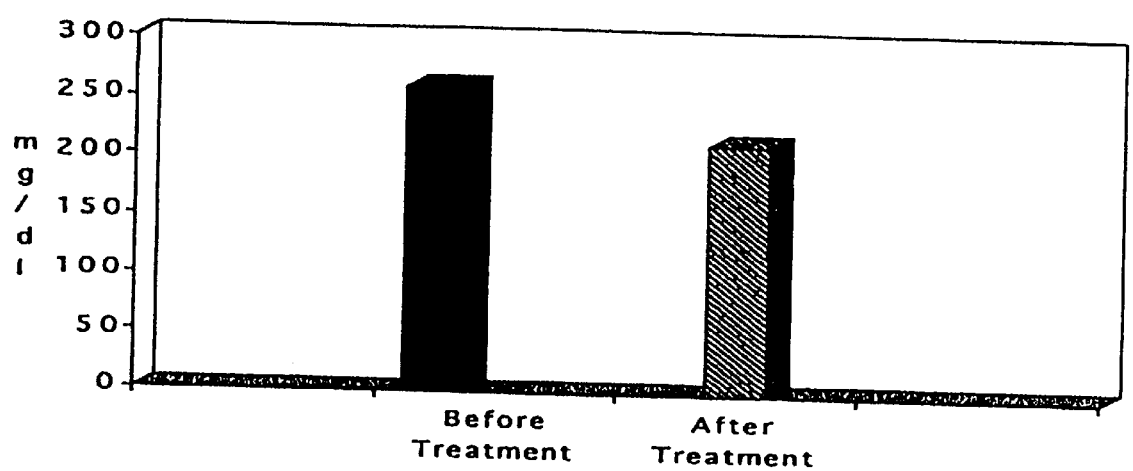
FIG. 4 is a graph showing change in cholesterol levels of human patients after administration of a preferred combination according to the present invention.

FIGS. 3 and 4 summarize experimental results of CR-201 (including experimental variants) in over a thousand human subjects. FIG. 3 shows reduction in mean serum triglyceride levels of about 45% (from 274.29 mg/dl to 150.71 mg/dl) and reduction in mean serum cholesterol levels of about 18% (from 260.7 mg/dl to 212.6 mg/dl).

The results set forth in FIGS. 3 and 4 strongly support the efficacy of CR-201 in reducing elevated serum triglyceride and cholesterol levels. The results also support the theory that a combination of herbs, some of which have substantial salutary effects on the circulatory system, and some of which primarily improve bowel motility, have an unexpectedly large positive effect on reducing serum triglyceride and cholesterol. Indeed, many combinations falling within these general guidelines are now expected to have similarly positive results.

It is contemplated that the claimed herbal combinations can be taken according to any acceptable protocol. At present the preferred form for the CR-201 combination is tablets, although gelatin or gelatin-like capsules, tinctures and other forms of administration are entirely possible. Presumably the various forms would include appropriate binders, excipients, stabilizers, flavorings and so forth.

Thus, while specific embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A herbal combination comprising Crataegus, Ho Shou Wu, Cassia Seed, Chrysanthemum, Lotus Leaf, Alisma, Hu-Zhang, and Rhubarb wherein; the Crataegus comprises approximately 20% (dry weight basis) of the combination; the Ho Shou Wu comprises approximately 12% (dry weight basis) of the combination; the Cassia Seed comprises approximately 15% (dry weight basis) of the combination; the Chrysanthemum comprises approximately 10% (dry weight basis) of the combination; the Lotus Leaf comprises approximately 10% (dry weight basis) of the combination; the Alisma comprises approximately 15% (dry weight basis) of the combination; the Hu-Zhang comprises approximately 10% (dry weight basis) of the combination; and the Rhubarb comprises approximately 8% (dry weight basis) of the combination.

* * * * *